(12) United States Patent
Chabloz

(10) Patent No.: US 10,639,174 B2
(45) Date of Patent: May 5, 2020

(54) VALVE FOR A PROSTHESIS SOCKET

(71) Applicant: CHABLOZ COMPOSANTS, Seyssinet-Pariset (FR)

(72) Inventor: Pierre Chabloz, Saint Georges de Commiers (FR)

(73) Assignee: CHABLOZ COMPOSANTS, Seyssinet-Pariset (FR)

( * ) Notice: Subject to any disclaimer, the term of this patent is extended or adjusted under 35 U.S.C. 154(b) by 0 days.

(21) Appl. No.: 15/593,851

(22) Filed: May 12, 2017

(65) Prior Publication Data

US 2017/0333226 A1 Nov. 23, 2017

(30) Foreign Application Priority Data

May 18, 2016 (FR) ...................... 16 54391

(51) Int. Cl.
- *A61F 2/80* (2006.01)
- *A61F 2/54* (2006.01)
- *A61F 2/60* (2006.01)
- *A61F 2/50* (2006.01)

(52) U.S. Cl.
CPC ...... *A61F 2/80* (2013.01); *A61F 2/54* (2013.01); *A61F 2/60* (2013.01); *A61F 2002/5001* (2013.01); *A61F 2002/543* (2013.01); *A61F 2002/802* (2013.01); *A61F 2002/805* (2013.01)

(58) Field of Classification Search
CPC .......... A61F 2002/748; A61F 2002/805; A61F 2002/807; A61F 2/80; F16K 7/16
See application file for complete search history.

(56) References Cited

U.S. PATENT DOCUMENTS

| | | | |
|---|---|---|---|
| 4,595,172 A | 6/1986 | Henderson | |
| 6,613,096 B1 | 9/2003 | Shirvis | |
| 9,089,444 B2 * | 7/2015 | Soss | A61F 2/78 |
| 2015/0265433 A1 | 9/2015 | Sandahl et al. | |

FOREIGN PATENT DOCUMENTS

| | | | | |
|---|---|---|---|---|
| DE | 605534 C | * | 11/1934 | ............... A61F 2/80 |
| DE | 2729800 A1 | * | 1/1979 | ........... A61F 2/7843 |
| EP | 623673 A2 | * | 3/1994 | |
| FR | 1 088 509 A | | 3/1955 | |
| FR | 2903294 A1 | | 1/2008 | |
| FR | 2903295 A1 | | 1/2008 | |
| FR | 2994381 A1 | | 2/2014 | |
| WO | 2014/035561 A1 | | 3/2014 | |

* cited by examiner

*Primary Examiner* — Christie L Bahena
(74) *Attorney, Agent, or Firm* — Oliff PLC

(57) ABSTRACT

Valve for a prosthesis socket, the socket delineating an open cavity to receive a stump of an amputated limb and delineating a pass-through hole opening into the cavity and designed to receive the valve, the valve including a support in which a pass-through channel is formed and an element movable between an outlet position in which the element allow an air flow out of the channel in an outlet direction and a sealing position in which the element prevent any air flow inside the channel in an opposite direction to the outlet direction, the support including a thread configured to mount the support in removable manner inside the pass-through hole, and to enable disassembly of the support in an opposite direction to the outlet direction.

6 Claims, 5 Drawing Sheets

VALVE FOR A PROSTHESIS SOCKET

BACKGROUND OF THE INVENTION

The invention relates to valves for a prosthesis socket, and more particularly to lower limb prostheses.

STATE OF THE ART

Prostheses designed to replace a missing part of an amputated limb, such as an arm or leg, are currently used. The prostheses comprise a socket, i.e. an engagement shell, on which a prosthetic limb is fixed. The socket delineates an open cavity to receive the stump of the amputated limb. Furthermore, in order to keep the socket secured to the stump, the residual air situated between the socket and the stump is expelled through a pass-through hole arranged in the socket. More particularly, a valve is housed in the pass-through hole to prevent air from getting into the cavity and to allow air to be expelled to the outside of the cavity. Such a valve is of the check valve, or one-way valve, type as it only enables an air flow in one direction in normal operation.

French Patent applications FR2903294 and FR2903295 can be cited for example which disclose a cap for a prosthesis, movable between a sealed position and a released position of a pass-through hole arranged in the prosthesis. The cap is equipped with a valve for performing air outlet from the cavity of the prosthesis and for preventing air from entering the cavity. The valve comprises a flexible element provided with an opening which is normally closed and which opens under the effect of a deformation of the flexible element caused by an air thrust originating from the cavity of the prosthesis.

French Patent application FR2994381 can also be cited which discloses a cap with an automatic check valve for a socket in the form of a negative pressure prosthesis shell comprising a fixing base equipped with a tubular end-part designed to be assembled to an aperture of the socket, and provided with a support element of the valve performing air outlet from the socket and preventing air from entering the socket. The support element is movable by pivoting to occupy a separated position where the valve is located away from the aperture, and the base is equipped with a securing nose of the support element. The valve is further clip-fastened onto the top part of the support element.

However these valve caps are not suitable for all types of prostheses. The prostheses can in fact be covered by a foam aesthetic covering and a covering stocking made from cloth, silicone, or polyurethane. Furthermore, the valves which have just been described are very sensitive to dust which prevents them from operating correctly. It is therefore necessary to clean the valves regularly, and the covering stocking and aesthetic covering then have to be removed to access the valves.

Patent documents US2015/0265433, FR1088509, WO2014/035561, U.S. Pat. Nos. 4,595,172, and 6,613,096 can be cited which disclose valves for a prosthesis socket for which the aesthetic covering has to be removed to clean the valve.

OBJECT OF THE INVENTION

The object of the invention consists in remedying these shortcomings, and more particularly in providing a valve that is easy to maintain and that guarantees that the junction between the socket and the stump of the amputated limb is kept secure.

Another object of the invention consists in providing a prosthesis socket equipped with one such valve.

According to one feature of the invention, a valve for a prosthesis socket is proposed, the socket delineating an open cavity to receive a stump of an amputated limb and delineating a pass-through hole opening into the cavity and designed to receive the valve.

The valve comprises a support in which a pass-through channel is formed, and an element mounted movable between an outlet position in which the element allows an air flow out of the channel in an outlet direction only and a sealing position in which the element prevents any air flow inside the channel in an opposite direction to the outlet direction.

The support comprises a fixing means configured to mount the support in removable manner inside the pass-through hole.

The fixing means is configured to enable disassembly of the support in the opposite direction to the outlet direction.

A valve is thus provided the element to be maintained of which may be extracted via the cavity of the socket. Maintenance of the valve is therefore facilitated as the aesthetic covering which envelops the socket does not have to be removed in order to be able to access the valve.

The valve can comprise a base configured to be mounted inside the pass-through hole and comprising a tapped hollow body, the fixing means comprising a thread cooperating with the thread of the body of the base.

The support can comprise a stop to prevent disassembly of the support in the outlet direction.

The valve can comprise an actuator configured to immobilize the element in the outlet position in order to allow an air flow out of the channel in the outlet direction and an air flow inside the channel in the opposite direction to the outlet direction.

The actuator can comprise a termination, and the support comprises a surface in which an opening of the channel and a longitudinal slot situated facing the terminal are formed, the longitudinal slot enabling a deformable part of the element to be received to move the element away from the opening of the channel.

The surface of the support can comprise two flat areas situated on each side of the longitudinal slot, the two flat areas being inclined with respect to one another.

The valve can comprise a cap having a deformable tab on which the actuator is mounted, the tab enabling movement of the actuator for the termination to press on the element.

The support can comprise a housing, the valve comprising a removable piece configured to cooperate with the housing in order to disassemble the support in the opposite direction to the outlet direction.

According to another feature, a prosthesis socket is proposed delineating an open cavity for receiving a stump of an amputated limb and delineating a pass-through hole in the cavity, the socket comprising a valve as defined in the foregoing mounted inside the pass-through hole.

BRIEF DESCRIPTION OF THE DRAWINGS

Other advantages and features will become more clearly apparent from the following description of particular embodiments of the invention given for non-restrictive example purposes only and represented in the appended drawings, in which.

DETAILED DESCRIPTION

Figure 1:
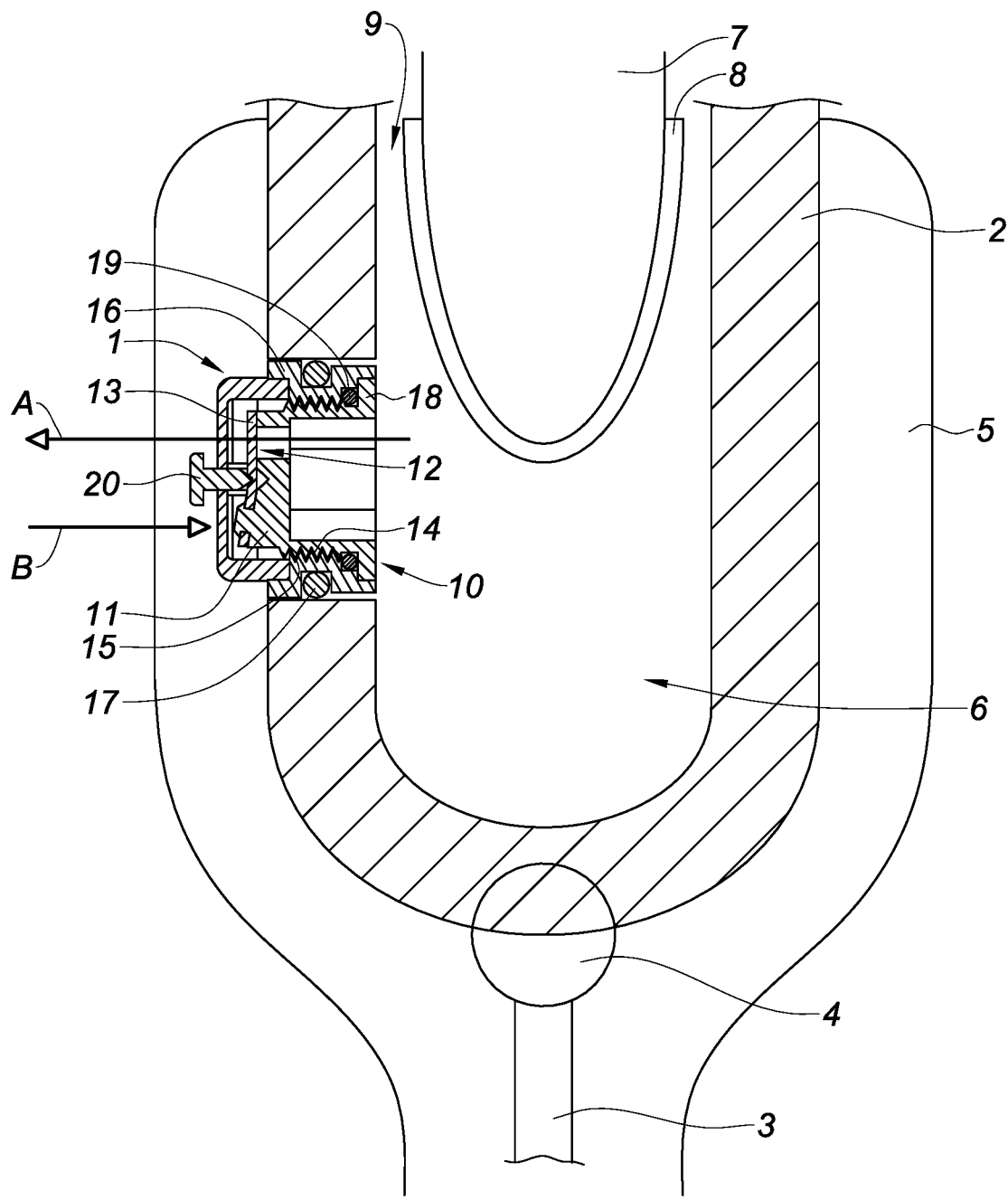
FIG. 1 schematically illustrates a cross-sectional view of an embodiment of a valve mounted on a prosthesis socket according to the invention.

In FIG. 1, a valve 1 for a prosthesis socket 2 has been represented. The prosthesis comprises a prosthetic limb 3, for example a replacement leg or forearm, fixed to a distal end of the socket 2 by an articulated link 4, such as a pivot joint. The prosthesis can also comprise an aesthetic covering 5 made from foam, cloth, silicone, or polyurethane, partially or totally covering the socket 2. The socket 2 delineates an open cavity 6 to receive a stump 7 of an amputated limb. The stump 7 of the amputated limb can be enveloped by a sleeve 8 of complementary external shape to the cavity 6 of the socket 2 to facilitate engagement of the stump 7 inside the cavity 6. An opening 9 of the cavity 6 is situated at the level of the proximal end of the socket 2. A pass-through hole 10 is further formed in the thickness of the socket 2. The pass-through hole 10 opens into the cavity 6 and is shaped so as to receive the valve 1.

The valve 1 is particularly suitable for a tibial prosthesis socket 2. The valve 1 enables a vacuum to be created between the socket 2 and stump 7, which maintains their junction. Preferentially, the valve 1 is a check valve, also called one-way valve, i.e. in normal operation, the valve 1 only lets air flow in a first direction A, in particular from the inside of the cavity 6 to the outside of the cavity 6, and prevents any air inlet inside the cavity 6 in a second direction B opposite the first direction A. The first direction A is also called "outlet direction", and the second direction B is called "disassembly direction" B. In order to keep the socket 2 secured to the stump 7, the residual air contained in the cavity 6 is expelled through the valve 1 to the outside of the cavity 6, in the first direction A. When the valve 1 is one-way, it prevents the outside air from entering the cavity 6, and a vacuum is then created between the stump 7 and socket 2 to keep them secured to one another. Advantageously, to guarantee the airtightness between the stump 7 and socket 2, a sealing part can be placed at the proximal end of the socket 2. For example, the sealing part can be a lip seal fixed to the socket 2, or to the sleeve 8 covering the stump 7, or be an elastic sheath enveloping the socket 2 and sleeve 7 at the level of the opening 9 of the cavity 6.

The valve 1 comprises a support 11 in which a channel 12 is formed, and an element 13 for closing the channel 12. The channel 12 is pass-through to make the inside of the cavity communicate with the outside. When the valve 1 is mounted in the pass-through hole 10, the pass-through channel 12 opens into the cavity 6 to enable the residual air situated between the socket 2 and stump 7 to be expelled. The element 13 of the valve 1 is movable between an outlet position in which the element 13 allows an air flow out of the pass-through channel 12 in the outlet direction A, and a sealing position, as illustrated in FIG. 1, in which the element 13 prevents any air flow inside the pass-through channel 12 in the disassembly direction B. The element 13 of the valve 1 is preferentially elastically deformable. In this case, the element 13 deforms in order to occupy the outlet position when the pressure of the air contained in the pass-through channel 12 is higher than the pressure of the outside air, and to revert to the sealing position when the pressure of the air contained in the pass-through channel 12 is lower than the pressure of the outside air. The element 13 can be mounted movable on the support 11. Preferentially, the element 13 comprises a first part mounted fixed on the support 11 and a second part movable with respect to the support 11. The element 13 can further be elastically deformable. For example, the element 13 can be an elastic membrane.

The support 11 also comprises a fixing means 14 configured to mount the support 11 inside the pass-through hole 10 in removable manner. More particularly, the fixing means 14 is configured to allow disassembly of the support 11 in the direction B opposite to outlet direction A. It is thus possible to dismantle the element 13 and its support 11 inside the cavity 6. A valve 1 whose support 11 and element 13 are dismantled in the disassembly direction B and are located inside the cavity 6 has been illustrated in FIG. 2. The aesthetic covering 5 then does not have to be disassembled to remove the element 13 from the socket 2. Such a valve 1 facilitates regular maintenance or repair. Furthermore, fixing means 14 enables the support 11 to be mounted in the outlet direction A. In other words, the support 11 is assembled to the socket 2 via the inside of the cavity 6, i.e. by inserting the support 11 and element 13 inside the cavity 6. This furthermore facilitates mounting thereof on a prosthesis previously equipped with an aesthetic covering 5, as the aesthetic covering 5 does not have to be removed to assemble the support 11 and element 13 to the socket 2.

For example, the fixing means 14 is configured to cooperate with a receiving means 15 to mount the support 11 in the pass-through hole 10. The receiving means 15 can be situated in the thickness of the socket 2. The support 11 can thus be mounted directly on the socket 2. Advantageously, the valve 1 can comprise a base 16 configured to be mounted in the pass-through hole 10 and to receive the support 11. The base 16 can be screw-fastened, welded, stuck, or crimped in the thickness of the socket 2. An O-ring 17 can be provided housed in an aperture provided on the outer surface of the base 16. The O-ring 17 guarantees the airtightness between the socket 2 and base 16. The base 16 comprises a hollow body. Furthermore, the base 16 comprises the receiving means 15 to mount the support 11 inside the hollow body of the base 16. When the base 16 is fixed to the pass-through hole 10, it prevents the support 11 from accidentally coming out when the stump 7 is removed from the cavity 6. For example, the fixing means 14 comprises an external thread and the receiving means 15 comprises an internal thread. The fixing means 14 can comprise securing notches and the receiving means 15 comprises housings designed to receive the securing notches.

Advantageously, the support 11 can comprise a stop 18 to prevent disassembly of the support 11 in the outlet direction A. The stop 18 can comprise a collar salient from the body of the support 11. The collar 18 is situated at a proximal end opposite to the distal end of the support 11 where the element 13 is located. The support 11 can also comprise an opening provided on its outer surface to receive an additional O-ring 19. The additional O-ring 19 guarantees the airtightness between the support 11 and base 16.

The valve 1 can further comprise an actuator 20 configured to immobilize the element 13 in the outlet position in order to allow both air flow out of the pass-through channel 12 in the outlet direction A and air flow inside the pass-through channel 12 in the disassembly direction B. When the element 13 is immobilized in the outlet position, an air inlet is allowed inside the cavity 6, which disunites the socket 2 and sleeve 7 so that the user can remove the prosthesis. It is also said that the actuator 20 unlocks the valve 1. Indeed, in normal operation, the valve 1 is said to be locked, and the element 13 is free to occupy the sealing position or the outlet position. The element 13 moves from one position to the other according to the pressure difference between the inside and outside of the cavity 6. On the contrary, it is noted that the valve 1 is unlocked when the element 13 is kept in the outlet position, and in this case air can flow in both directions A, B between the inside and outside of the cavity 6.

Figure 2:
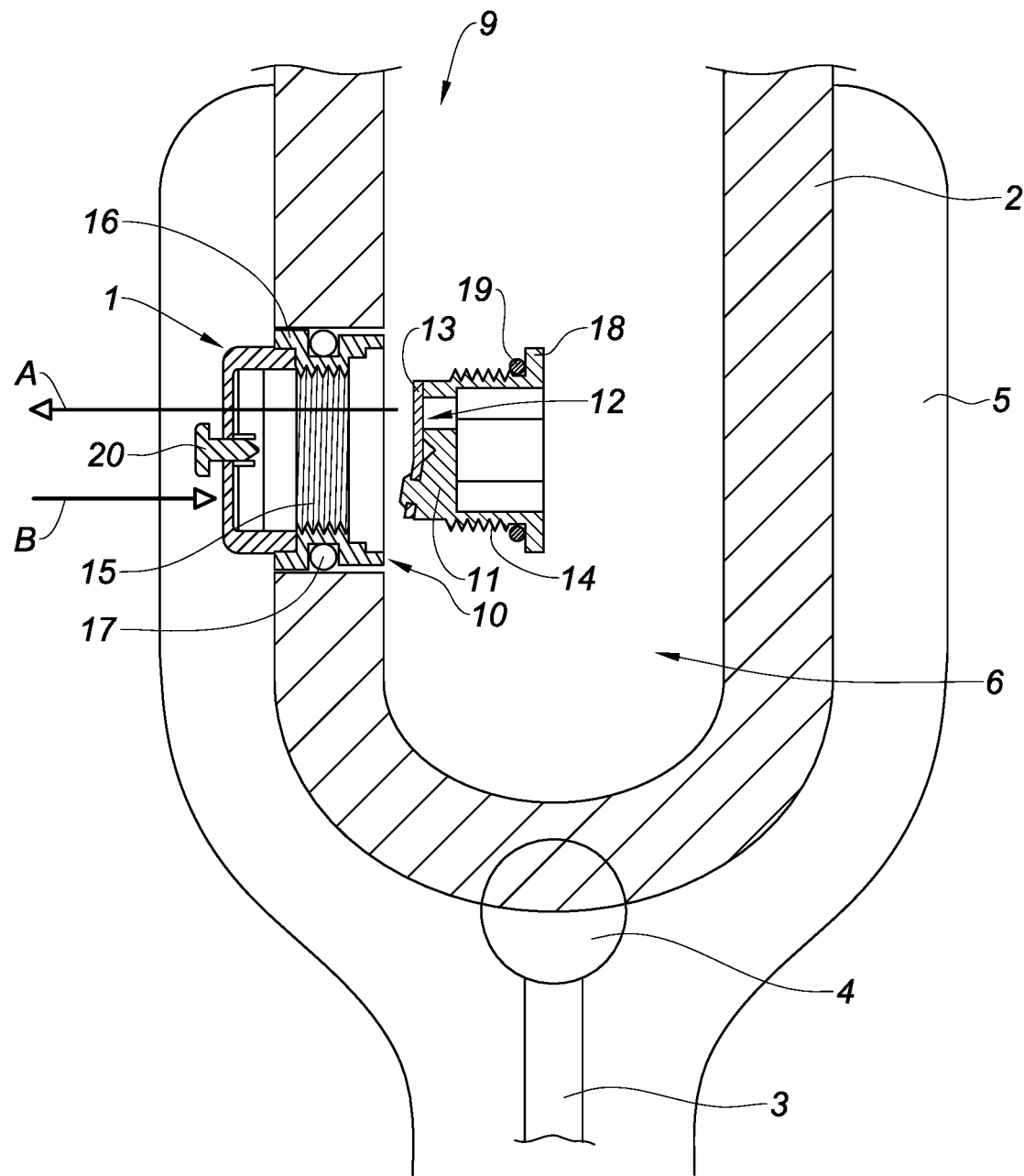
FIG. 2 schematically illustrates a cross-sectional view of the valve of FIG. 1 the support of which has been dismantled.
Figures 4, 5:
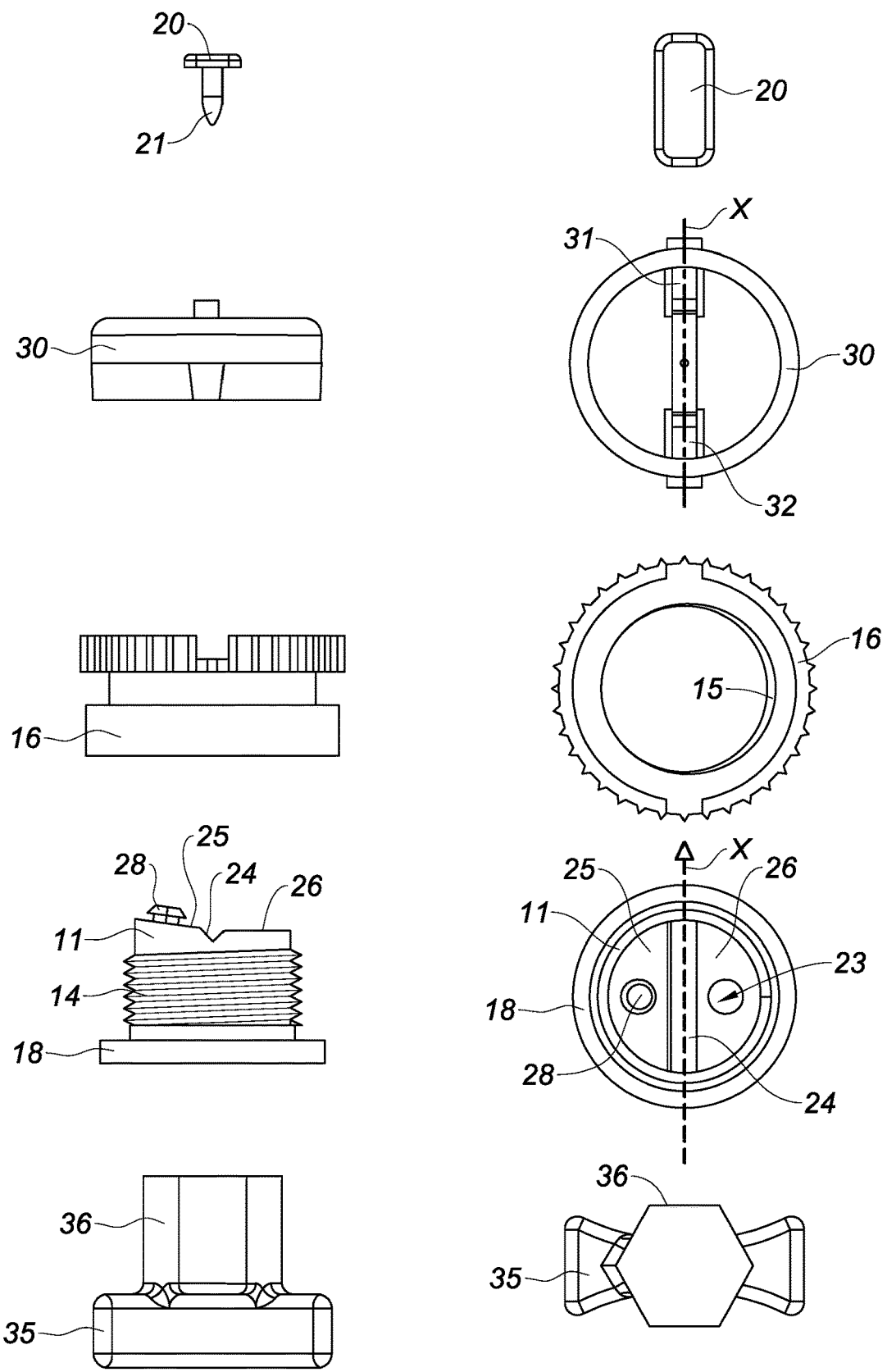
FIG. 4 schematically illustrates perspective side views of certain parts of FIG. 3.
FIG. 5 schematically illustrates perspective top views of the parts of FIG. 4.
Figure 6:
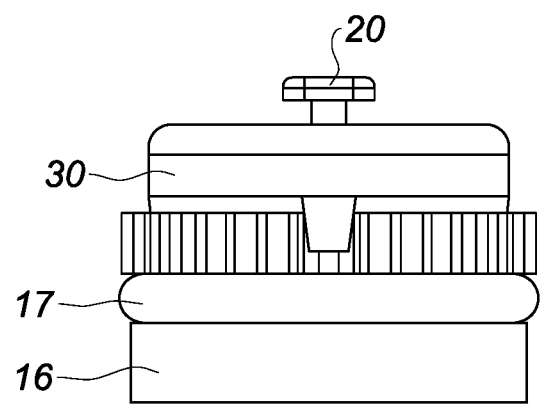
FIG. 6 schematically illustrates a perspective side view of the valve of FIG. 3 the parts of which are mounted.
Figure 7:
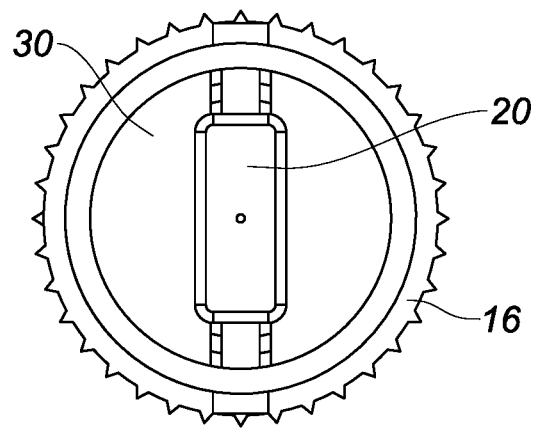
FIG. 7 schematically illustrates a perspective top view of the valve of FIG. 6.

In FIG. 2, the valve 1 described in FIG. 1 has been represented, the support 11 of which is removed from the base 16, i.e. removed from the socket 2. In FIGS. 4 and 5, the valve 1 has been represented with its parts disassembled, and in FIGS. 6 and 7, the valve 1 has been represented with its parts assembled.

Figure 3:
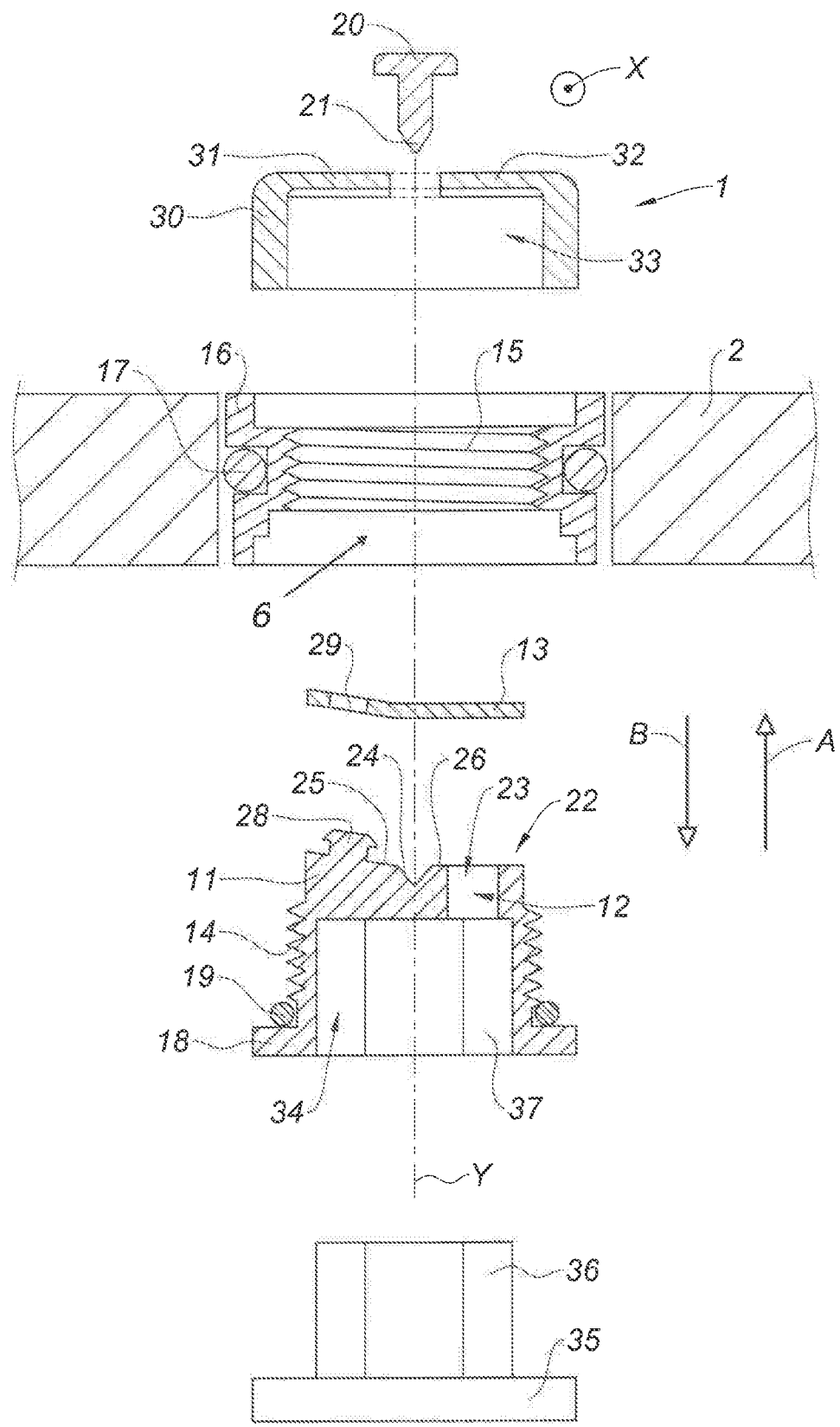
FIG. 3 schematically illustrates an exploded cross-sectional view of another embodiment of the different parts of a valve.
Figure 8:
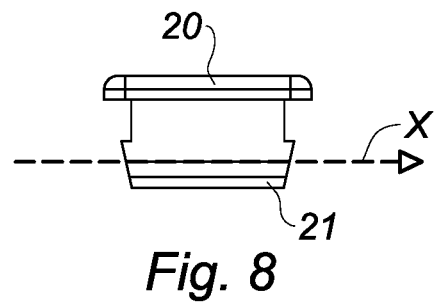
FIG. 8 schematically illustrates another perspective side view of a valve actuator.

In FIG. 3, an exploded view of the different parts of the valve 1 has been represented. Preferably, the actuator 20 comprises a termination 21 and the support 11 comprises a surface 22 in which an opening 23 of the pass-through channel 12 and a slot 24 are formed. The surface 22 is situated at the distal end of the support 11. The slot 24 preferably has a complementary shape to that of the termination of the actuator 20 to receive a deformed part of the element 13. For example, the termination 21 of the actuator 20 extends along a longitudinal axis X, perpendicular to the sheet plane of FIG. 3. In FIG. 8, another view of the actuator 20 has been represented in which the longitudinal axis X is in the plane of FIG. 8. The termination 21 can have a V-shape to provide an end in the shape of a tip. The longitudinal slot 24 also extends along an axis parallel to the longitudinal axis X of the termination 21. The slot 24 can also have a V-shape complementary to that of the termination 21. In particular, the longitudinal slot 24 is situated facing the termination 21. When the actuator 20 occupies an initial position, as illustrated in FIG. 1, the valve 1 is locked. When the user presses the actuator 20, the latter translates along an axis Y parallel to a longitudinal axis of the pass-through channel 12. When translation takes place, the actuator 20 presses the element 13 against the surface 22 of the support 11, in particular at the level of the longitudinal slot 24. In this way, a deformable part of the element 13 is inserted into the slot 24, which raises the element 13 and moves the latter away from the opening 23 of the pass-through channel 12. At the end of translation, the actuator 20 occupies the second position in which the element 13 occupies the outlet position. The element 13 can then be kept in the outlet position by maintaining the pressure of the actuator 20 against the element 13. When the element 13 is immobilized in the outlet position, air can flow from the cavity 6 to the outside, through the pass-through channel 12, and in the opposite direction, i.e. from the outside to the inside of the cavity 6. When the user releases the pressure on the actuator 20, the latter reverts to its initial position and the element 13 reverts to its sealing position. The element 13 reverts to its position on account of its elasticity.

In order to facilitate deformation of the element 13 so that it occupies the outlet position, the surface 22 of the support 11 can comprise two flat areas 25, 26 situated on each side of the longitudinal slot 24. The two flat areas 25, 26 can be inclined with respect to one another. Furthermore, the element 13 can have a curved shape which coincides with the two inclined flat areas 25, 26. The support 11 can comprise a spigot 28 which is inserted in an aperture 29 provided in the element 13. The spigot 28 enables a part of the element 13 to be kept fixed to keep the element 13 secured to the support 11, the other part of the element 13 being deformable to occupy the outlet and sealing positions.

Advantageously, the valve 1 comprises a cap 30 having at least one deformable tab 31, 32 on which the actuator 20 is mounted. The deformable tabs allow movement of the actuator 20 in translation along the axis Y to press the actuator 20 against the element 13. For example, the tabs are elastic and the actuator 20 reverts to its initial position on account of the elasticity of the tabs 31, 32. According to another advantage, the cap 31 delineates a chamber 33. The chamber 33 is situated at one end of the valve 1 so that the element 13 is situated between the chamber 33 and support 11. The chamber 33 enables the element 13 to occupy the outlet position. The chamber 33 in fact forms a clearance volume to receive the element 13. Furthermore, a pass-through hole is formed in the wall of the cap 30. The pass-through hole is situated on the surface of the cap 30 where the tabs 31, 32 are located. The pass-through hole opens into the chamber 33 to allow the outside air to enter the chamber 33, and inversely so that the air from chamber 33 can flow to the outside.

When the user wants to remove the stump 7 from the socket 2, after the vacuum has been created between the socket 2 and stump 7, the user presses the actuator 20, the element 13 is immobilized in the outlet position, and the outside air is inserted inside the cavity 6. This air inserted inside the cavity 6 disunites the stump 7 and socket 2, and the stump 7 can be removed. For example, the aesthetic covering 5 can be porous to air. In this way, when it is required to create the vacuum between the socket 2 and stump 7, the aesthetic covering 5 allows the residual air situated between the socket 2 and stump 7 to escape the outside. Furthermore, when it is required to remove the stump 7 from the socket 2, the aesthetic covering 5 enables the outside air to be inserted inside the cavity 6. As a variant, an air outlet channel can be provided situated in the thickness of the aesthetic covering 5 and connecting the chamber 33 with the outside. In particular, the outlet channel connects the pass-through hole of the cap 30 with the outside. Advantageously, the aesthetic covering 5 is flexible to allow the user to press the actuator 20, from the outside, by pressing the aesthetic covering 5.

The support 11 can also comprise a housing 34 designed to receive a removable piece 35. The piece 35 is inserted in the housing 34, and cooperates with the housing 34 to disassemble the support 11 in the disassembly direction B. For example, the piece 35 can comprise several faces 36 and the housing 34 comprises complementary faces 37 to be able to make the support 11 rotate around the axis Y, thereby disassembling the support 11 from the valve 1.

The invention claimed is:

1. A valve for a prosthesis socket, the socket delineating an open cavity to receive a stump of an amputated limb and delineating a pass-through hole opening into the cavity and designed to receive the valve, the valve comprising:
   a support in which a pass-through channel is formed, an element mounted movable between an outlet position in which the element allows an air flow out of the channel in an outlet direction only and a sealing position in which the element prevents any air flow inside the channel in an opposite direction to the outlet direction, a base configured to be mounted inside the pass-through hole and comprising a hollow body and a receiving means, the support comprising a fixing means configured to cooperate with the receiving means to mount the support in removable manner inside the pass-through hole, the fixing means being configured to enable disassembly of the support in the opposite direction to the outlet direction, and an actuator configured to immobilize the element in the outlet position in order to allow an air flow out of the channel in the outlet direction and an air flow inside the channel in the opposite direction to the outlet direction, the actuator comprising an end, and the support comprises a surface in which an opening of the channel and a longitudinal slot situated facing the end are formed, the longitudinal slot enabling a deformable part of the element to be received to move the element away from the opening of the channel.

2. The valve according to claim 1, wherein the support comprises a stop to prevent disassembly of the support in the outlet direction.

3. The valve according to claim 1, wherein the surface of the support comprises two flat areas situated on each side of the longitudinal slot, the two flat areas being inclined with respect to one another.

4. The valve according to claim 1, comprising a cap having a deformable tab on which the actuator is mounted, the tab enabling movement of the actuator for the end to press on the element.

5. The valve according to claim 1, wherein the support comprises a housing, the valve comprising a removable piece configured to cooperate with the housing in order to disassemble the support in the opposite direction to the outlet direction.

6. A prosthesis socket delineating an open cavity for receiving a stump of an amputated limb and delineating a pass-through hole in the cavity, the socket comprising a valve according to claim 1 mounted inside the pass-through hole.

* * * * *